United States Patent [19]

Nowatari et al.

[11] Patent Number: 4,861,905
[45] Date of Patent: * Aug. 29, 1989

[54] PLATINUM COMPLEXES

[75] Inventors: Hiroyoshi Nowatari; Hiroshi Hayami, both of Takasaki; Yasuo Kuroda, Gunma; Sumio Yoda, Takasaki; Katsutoshi Takahashi, Tokyo, all of Japan

[73] Assignee: Nippon Kayaku Kabushiki Kaisha, Tokyo, Japan

[*] Notice: The portion of the term of this patent subsequent to Sep. 5, 2006 has been disclaimed.

[21] Appl. No.: 91,034

[22] Filed: Aug. 31, 1987

[30] Foreign Application Priority Data

Feb. 19, 1987 [JP] Japan .................................. 62-34512

[51] Int. Cl.$^4$ ................................................ C07F 9/68
[52] U.S. Cl. ........................................ 556/40; 556/137
[58] Field of Search .................. 556/137, 40; 514/492, 514/908

[56] References Cited

U.S. PATENT DOCUMENTS

| | | |
|---|---|---|
| 4,250,189 | 2/1981 | Hydes et al. |
| 4,255,347 | 3/1981 | Kidani et al. |
| 4,410,544 | 10/1983 | Berg et al. |
| 4,431,666 | 2/1984 | Bulten et al. |
| 4,466,924 | 8/1984 | Verbeek et al. |
| 4,477,387 | 10/1984 | Kidani et al. |
| 4,482,569 | 11/1984 | Bulten et al. |
| 4,500,465 | 2/1985 | Amundsen et al. |
| 4,562,275 | 12/1985 | Speer et al. |
| 4,598,091 | 7/1986 | Schonenberger et al. |
| 4,607,114 | 8/1986 | Nakayama et al. |

FOREIGN PATENT DOCUMENTS

| | | | |
|---|---|---|---|
| 0098135 | of 0000 | European Pat. Off. | 556/137 |
| 0055300 | 7/1982 | European Pat. Off. | |
| 156416 | 9/1982 | Japan | |

OTHER PUBLICATIONS

Ing, in Process in Drug Research, vol. 7, edited by Ernst Juckner, Basel, 1964, Birkhauser Verlag, pp. 306–307.
Chemical Abstracts, 93 125415r (1980).
Chemical Abstracts, 95 423b (1981).
Chemical Abstracts, vol. 88, No. 20, Abstract No. 144630v.
Inorganica Chimica Acta, 26 (1978) L13–L14, Pahor et al.
Broomhead, J. A., et al., Chem.-Biol. Interactions, 31 (1980):133–132.

Primary Examiner—Donald B. Moyer
Assistant Examiner—Stuart L. Hendrickson
Attorney, Agent, or Firm—Banner, Birch, McKie & Beckett

[57] ABSTRACT

A diamine platinum (II) complex represented by the general formula

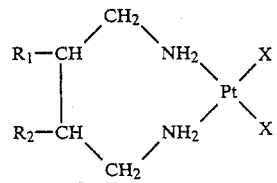

[wherein $R_1$ and $R_2$ are each a lower alkyl group; and two X's are each a halogen atom or jointly form a group represented by

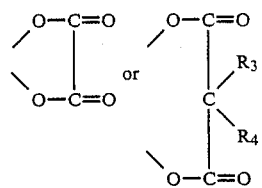

(wherein $R_3$ and $R_4$ are each a hydrogen atom or a lower alkyl group) or a group represented by

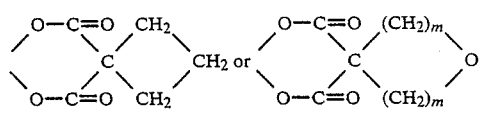

(wherein m is 1 or 2)].

4 Claims, No Drawings

PLATINUM COMPLEXES

BACKGROUND OF INVENTION

1. Field of the Invention

This invention relates to novel platinum complexes having an antitumor effect.

2. Description of the Prior Art

With respect to platinum complexes having an antitumor effect, cis-Platin (cis-dichlorodiammineplatinum) is already available commercially and is being applied to many casess because of its striking effect. Other platinum complexes having an antitumor effect as well are reported in several papers. Of these, platinum complexes having a straight alkyl diamine as a ligand are limited to those having a ligand repesented by the general formula $$H_2N-C_nR_{2n}-NH_2 \quad (I)$$

(wherein R is a hydrogen atom or a substituent such as an alkyl group, a hydroxyl group or the like and n is in an integer of 1 to 3), except for a few complexes described in Inorg. Chem. Acta, 26 (1978) L13-L14. Kidani et al. also described the comlexes having the diamine ligand represented by the general formula (II), in U.S. Pat. No. 4,477,387(1984).

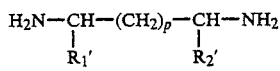

(wherein $R_1'$ and $R_2'$ are the same or different and each is hydrogen, an alkyl group or an aryl group, and p is 0 or in an integer of 1 to 3). But, of these, the complexes which have the diamine ligand represented by the general formula (II) wherein p is 2 or 3, were not characterized by any analysis or biological test, at all.

As mentioned above, cis-Platin is commercially available as a platinum complex carcinostatic agent. However, cis-Platin has high renal toxicity, which possess a dose limiting factor. Therefore, in administering cisPlatin, it is requisite that a large amount of water be administered before and during the administration of cisPlatin and that cis-Platin be administered together with a diuretics and over a long period of time. Further, cisPlatin, having low solubility in water and dissolving in water slowly, is supplied at a very low concentration. Furthermore, cis-Platin has very high vomiting toxicity, posing a problem in cure. Because of these drawbacks of cis-Platin, many researches have been conducted in order to find a platinum complex having an antitumor activity which has high solubility in water, low renal toxicity and low vomiting toxicity. However, no platinum complex has been applied practically till now.

SUMMARY OF INVENTION

When a 2,3-dimethyl-1,4-butanediamine reacts with a platinum atom to form a coordination compound through the two nitrogen atoms of the diamine, there is formed a ring structure by 7 atoms including the platinum atom, namely 7-membered ring structure as shown in the formula (III) which appears later. In general, complexes having such a 7-membered ring structure are very difficult to synthesize in the usual way. As a result of an extensive research, the present inventors succeeded in the synthesis of various platinum complexes having a 2,3-dimethyl-1,4-butanediamine as a ligand and found that these complexes have an antitumor effect and that their renal toxicity and vomiting toxicity are remarkably lower than those of cis-Platin.

The present invention has been completed based on the above finding.

The present invention relates to 2,3-dimethyl-1,4-butanediamine platinum (II) complexes represented by the general formula (III)

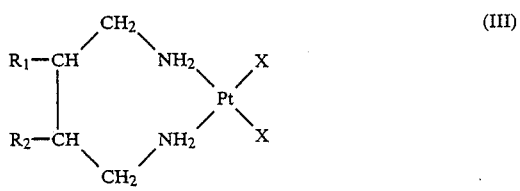

[wherein $R_1$ and $R_2$ are each a lower alkyl group; and two X's are each a halogen atom or jointly form a group represented by

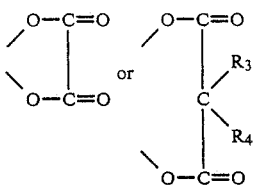

(wherein $R_3$ and $R_4$ are each a hydrogen atom or a lower alkyl group) or a group represented by

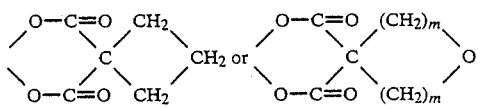

(wherein m is 1 or 2)].

DETAILED DESCRIPTION OF THE INVENTION

In the above general formula (III), the lower alkyls represented by $R_1$, $R_2$, $R_3$ and $R_4$ include, for example, alkyl groups of 1 to 4 carbon atoms. Specifically, there are mentioned a methyl group, an ethyl group, an n-propyl group, an isopropyl group, etc.

In the general formula (III), the halogen atom represented by X include Cl, Br, etc.

Of the compounds of the present invention represented by the formula (III), preferable are those where two X's jointly form a group represented by

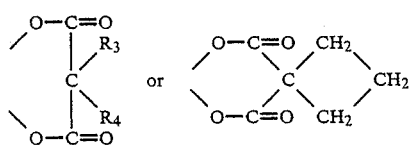

Typical examples of the compounds represented by the general formula (III) are shown below. However, the present invention is not restricted to these Examples.

1. cis-Dichloro-2,3-dimethyl-1,4-butanediamine platinum.

2. cis-Oxalato-2,3-dimethyl-1,4-butanediamine platinum.

3. cis-Malonato-2,3-dimethyl-1,4-butanediamine platinum.

4. cis-Cyclobutane-1,1-dicarboxylato-2,3-dimethyl-1,4-butanediamine platinum.

5. cis-Dimethylmalonato-2,3-dimethyl-1,4-butanediamine platinum.

6. cis-4-Oxacyclohexane-1,1-dicarboxylato-2,3-dimethyl-1,4-butanediamine platinum.

7. cis-Ethylmalonato-2,3-dimethyl-1,4-butanediamine platinum.

8. cis-Diethylmalonato-2,3-dimethyl-1,4-butanediamine platinum.

9. cis-Dichloro-2,3-diethyl-1,4-butanediamine platinum.

The compounds of the present invention can be produced by utilizing a known process, for example, a process described in Indian J. Chem., 8, 193(1970) but it is necessary to modify the reaction method.

The compounds of the present invention can be produced by reacting a diamine represented by the general formula

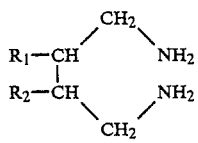

(wherein $R_1$ and $R_2$ have the same definition as given previously, rspectively) with $M_2Pt(Hal)_4$ (where M is an atom capable of becoming a monovalent cation and Hal is a halogen atom) to obtain a dihalogenodiamine platinum complex represented by the general formula

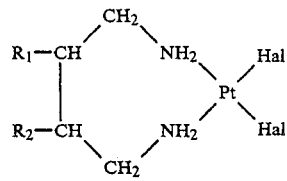

(wherein $R_1$ and $R_2$ and Hal have the same definitions as given previously, respectively) and, as necessary, reacting the dihalogenodiamine platinum complex with silver ions in the presence of water to convert to a diaquacomplex and reacting the diaquacomplex with a dicarboxylic acid or a salt thereof.

The production process of the compounds of the present invention will be described in more detail.

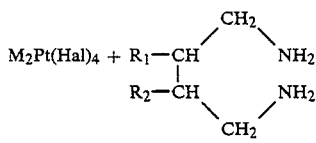

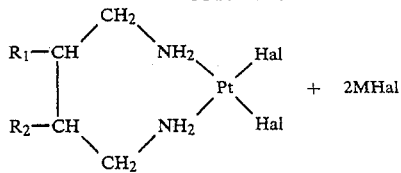

(IIIa)

(In the above, M is an atom capable of becoming a monovalent cation, such as Na, K, Cs, or the like; Hal is a halogen atom such as Cl, Br, I, or the like; $R_1$ and $R_2$ have the same definitions as given previously, respectively.)

As shown in the above reaction scheme, a tetrahalogenoplatinate and diamine are reacted in an aqueous medium, preferably water to obtain a dihalogenodiamine platinum. Water is used in an amount of preferably 5 to 500 liters, more preferably 5 to 160 liters, particularly preferably 20 to 80 liters per 1 mole of the tetrahalogenoplatinate. The diamine is used in an amount of preferably 0.5 to 4 moles, particularly preferably 0.9 to 1.2 moles per 1 mole of the tetrahalogenoplatinate. This reaction is conducted at 0° to 100° C., preferably 50° to 70° C. with stirring. In conducting the reaction, it is preferable that an aqueous tetrahalogenoplatinate solution and an aqueous diamine solution are gradually added to distilled water separately at the same time. The addition is conducted preferably slowly and usually takes 1 to 6 hours. The reaction can be conducted in an atmosphere of air but preferably under a stream of an inert gas such as nitrogen or the like.

Next, as shown in the following reaction scheme, the dihalogenodiamine platinum (IIIa) is suspended in water and reacted with silver ions and the resulting silver halide precipitate is removed by filtration to obtain an aqueous solution of a diaquacomplex (IV).

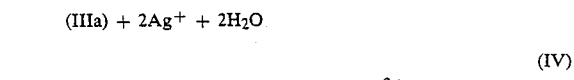

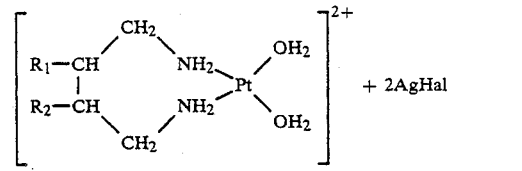

The water for suspending the dihalogenodiamine complex (IIIa) can be used in an appropriate amount but the amount preferably is 5 to 150 liters per 1 mole of the complex (IIIa). The amount of silver ion has no particular restriction but, from an economic standpoint, is preferred to be 0.5 to 6 equivalents per 1 equivalent of the dihalogenodiamine complex (IIIa). In order to avoid an excessive addition, the amount particularly preferably is 1.9 to 2 equivalents per 1 equivalent of the dihalogenodiamine complex (IIIa). The reaction is conducted at 0° to 100° C., preferably 60° to 80° C. with stirring. As the compound generating silver ion, there can be used, for example, silver nitrate, silver sulfate, silver perchlorate and silver acetate.

Finally, the diaquacomplex (IV) is reacted with a dicarboxylic acid salt, a dicarboxylic acid monohydrogen salt or a dicarboxylic acid. For example, the reaction is carried out by adding an aqueous solution containing an appropriate amount of a dicarboxylic acid salt, a dicarboxylic acid monohydrogen salt or a dicarboxylic acid to the aqueous solution of the diaquacomplex (IV). Said salt or acid is used in an amount of preferably 0.5 to 10 moles, particularly preferably 0.9 to 6 moles per 1 mole of the diaquacomplex (IV). The reaction can be conducted at 0° to 100° C. but preferably is conducted at 40° to 90° C. to obtain a compound (IIIb).

(IV) + Dicarboxylic acid salt or dicarboxylic acid monohydrogen salt or dicarboxylic acid

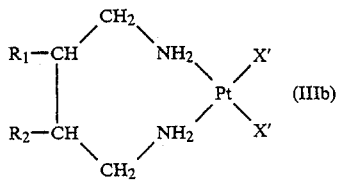

(IIIb)

(In the above, X' is same as X other than halogen atoms.)

The structure of the compounds (III) of the present invention was confirmed by various analytical methods such as elemental analysis, infrared absorption spectrometry, fast atom bombardment mass spectrometry (FABMS Pt$^{194}$) and the like.

The compounds of the present invention have very low renal toxicity and very low vomiting toxicity, have high solubility in water, are dissolved in water radidly, have an excellent antitumor effect, and accordingly are useful as an antitumor agent. When they are used as an antitumor agent, they can be administered as an injection, an oral drug and the like. Moreover, the compounds of the present invention are stable in air at room temperature, thus requiring no low temperature storage.

The embodiments of the present invention will be described below by way of Examples. However, the present invention is in no way restricted to these Examples.

EXAMPLE 1 cis-Dichloro-2,3-dimethyl-1,4-butanediamine Platinum (Compound No. 1)

10 g of potassium tetrachloroplatinate (II) was dissolved in 350 ml of water. Thereto was added a solution of 16 g of potassium iodide dissolved in 50 ml of water, with stirring. Stirring was continued for 5 minutes at 35° C. to obtain a black aqueous solution of potassium tetraiodoplatinate (II). Separately, 2.80 g of 2,3-dimethyl-1,4-butanediamine was disssolved in 400 ml of water to obtain an aqueous 2,3-dimethyl-1,4-butanediamine solution. 250 ml of water was placed in a flask then stirred at 60° C. under nitrogen atmosphere. Into this water, were dropwise added the aqueous potassium tetraiodoplatinate (II) solution and the aqueous 2,3-dimethyl-1,4-butanediamine solution both prepared above, simultaneously for 2 hours at the constant rates, respectively. The reaction was carried out with stirring at 60° C. The resulting reddish brown crystals were collected by filtration and washed with water, ethanol and ether in this order. The crystals were then dried under vacuum to obtain 10.13 g (yield: 74.4%) of crystals of cisdiiodo-2,3-dimethyl-1,4-butanediamine platinum.

1 g of this product was suspended in 20 ml of water. Thereto was added a solution of 589 mg of silver nitrate dissolved in 10 ml of water. They were stirred for 20 minutes at 60° C. for reaction. The reaction mixture was cooled to room temperature and filtrated to remove silver iodide. The silver iodide removed was washed with water. The filtrate and the washings were mixed together, and thereto was added a solution of 620 mg of sodium chloride dissolved in 5 ml of water. The mixture was stirred for 10 minutes at room temperature. The resulting yellow crystals were collected by filtration, washed with a small amount of water of 0° C. and then with ethanol, and dried under vacuum to obtain a compound No. 1.

Yield: 299 mg;
Elementary analysis
Calculated (%): C, 18.86; H, 4.22; N, 7.32; Pt, 51.04; Found (%): C, 18.63; H, 4.39; N, 7.18; Pt, 50.6; FAB-MS: (M+H)$^+$=381.

EXAMPLE 2 cis-Oxalato-2,3-dimethyl-1,4-butanediamine Platinum (Compound No. 2)

In Example 1, 620 mg of sodium chloride was replaced by 652 mg of potassium oxalate monohydrate. After addition of a solution of 652 mg of this potassium oxalate monohydrate in 5 ml of water, the resulting mixture was stirred for 2 hours at 60° C. The resulting mixture was concentrated to 5 ml and then cooled to 0° C. The resulting white crystals were collected by filtration, washed with a small amount of water of 0° C. and then with ethanol, and dried under vacuum to obtain a compound No. 2.

Yield: 398 mg; Elementary analysis Calculated (%): C, 24.06; H, 4.04; N, 7.02; Pt, 48.85; Found (%): C, 24.22; H, 4.28; N, 7.31; Pt, 49.0; FAB-MS: (M+H)$^+$=399.

EXAMPLE 3 cis-Malonato-2,3-dimethyl-1,4-butanediamine Platinum (Compound No. 3)

In Example 1, the solution of 620 mg of sodium chloride dissolved in 5 ml of water was replaced by a solution obtained by dissolving 368 mg of malonic acid in 6.37 ml of 1 N aqueous sodium hydroxide solution. The mixture resulting from addition of this solution was stirred for 3 hours at 50° C. for reaction. The reaction mixture was concentrated to 5 ml and then cooled to 0° C. The resulting white crystals were collected by filtration, washed with a small amount of water of 0° C. and then with ethanol, and dried under vacuum to obtain a compound No. 3.

Yield: 243 mg; Elementary analysis Calculated (%): C, 26.15; H, 4.39; N, 6.78; Pt, 47.20; Found (%): C, 26.40; H, 4.11; N, 6.65; Pt, 47.9; FAB-MS: (M+H)$^+$=413.

EXAMPLE 4 cis-Cyclobutane-1,1-dicarboxylato-2,3-dimethyl-1,4-butanediamine Platinum (Compound No. 4)

In Example 1, the solution of 620 mg of sodium chloride dissolved in 5 ml of water was replaced by a solution obtained by dissolving 510 mg of 1,1-cyclobutanedicarboxylic acid in 6.90 ml of 1 N aqueous sodium hydroxide solution. The mixture resulting from addition of this solution was stirred for 2 hours at 60° C. for reaction. The reaction mixture was concentrated to 5 ml and then cooled to 0° C. The resulting white crystals were collected by filtration, washed with a small amount of water of 0° C. and then with ethanol, and dried under vacuum to obtain a compound No. 4.

Yield: 330 mg; Elementary analysis Calculated (%): C, 31.79; H, 4.89; N, 6.18; Pt, 43.03; Found (%): C, 32.01; H, 4.67; N, 6.34; Pt, 44.0; FAB-MS: $(M+H)^+ = 453$.

EXAMPLE 5 cis-Dimethylmalonato-2,3-dimethyl-1,4-butanediamine Platinum (Compound No. 5)

In Example 1, the solution of 620 mg of sodium chloride dissolved in 5 ml of water was replaced by a solution obtained by dissolving 468 mg of dimethylmalonic acid in 6.90 ml of 1 N aqueous sodium hydroxide solution. The mixture resulting from addition of this solution was stirred for 2 hours at 60° C. for reaction. The reaction mixture was concentrated to 5 ml and then cooled to 0° C. The resulting white crystals were collected by filtration, washed with a small amount of water of 0° C. and then with ethanol, and dried under vacuum to obtain a compound No. 5.

Yield: 230 mg; Elementary analysis Calculated (%): C, 29.93; H, 5.02; N, 6.35; Pt, 44.20; Found (%): C, 30.11; H, 5.30; N, 6.08; Pt, 44.9; FAB-MS: $(M+H)^+ = 441$.

EXAMPLE 6 cis-4-Oxacyclohexane-1,1-dicarboxylato-2,3dimethyl-1,4-butanediamine Platinum (Compound No. 6)

In Example 1, the solution of 620 mg of sodium chloride dissolved in 5 ml of water was replaced by a solution obtained by dissolving 616 mg of 4-oxacyclohexane1,1-dicarboxylic acid in 6.90 ml of 1 N aqueous sodium hydroxide solution. The mixture resulting from addition of this solution was stirred for 2 hours at 60° C. for reaction. The reaction mixture was concentrated to 5 ml and then cooled to 0° C. The resulting white crystals were collected by filtration, washed with a small amount of water of 0° C. and then with ethanol, and dried under vacuum to obtain a compound No. 6.

Yield: 252 mg; Elementary analysis

Calculated (%): C, 32.30; H, 5.00; N, 5.79; Pt, 40.35; Found (%): C, 32.48; H, 4.86; N, 5.92; Pt, 41.4; FAB-MS: $(M+H)^+ = 483$.

EXAMPLE 7 cis-Ethylmalonato-2,3-dimethyl-1,4-butanediamine Platinum (Compound No. 7)

In Example 1, the solution of 620 mg of sodium chloride dissolved in 5 ml of water was replaced by a solution obtained by dissolving 468 mg of ethylmalonic acid in 6.90 ml of 1 N aqueous sodium hydroxide solution. The mixture resulting from addition of this solution was stirred for 2 hours at 60° C. for reaction. The reaction mixture was concentrated to 5 ml and then cooled to 0° C. The resulting white crystals were collected by filtration, washed with a small amount of water of 0° C. and then with ethanol, and dried under vacuum to obtain a compound No. 7.

Yield: 307 mg; Elementary analysis Calculated (%): C, 29.93; H, 5.02; N, 6.35; Pt, 44.20; Found (%): C, 30.01; H, 4.98; N, 6.16; Pt, 43.7; FAB-MS: $(M+H)^+ = 441$.

EXAMPLE 8 cis-Diethylmalonato-2,3-dimethyl-1,4-butanediamine Platinum (Compound No. 8)

In Example 1, the solution of 620 mg of sodium chloride dissolved in 5 ml of water was replaced by a solution obtained by dissolving 567 mg of diethylmalonic acid in 6.90 ml of 1 N aqueous sodium hydroxide solution. The mixture resulting from addition of this solution was stirred for 2 hours at 60° C. for reaction. The reaction mixture was concentrated to 5 ml and then cooled to 0° C. The resulting white crystals were collected by filtration, washed with a small amount of water of 0° C. and then with ethanol, and dried under vacuum to obtain a compound No. 8.

Yield: 383 mg; Elementary analysis Calculated (%): C, 33.26; H, 5.58; N, 5.97; Pt, 41.56; Found (%): C, 33.08; H, 5.26; N, 6.01; Pt, 40.6; FAB-MS: $(M+H)^+ = 469$.

The physical characteristics of the compounds of the present invention are shown in Table 1.

TABLE 1

| Compound No. | Solubility in water (mg/ml) | IR absorption spectrum $(cm^{-1})$ | |
|---|---|---|---|
| | | N-H | C=O |
| 1 | >2* | 3230-3130 | — |
| 2 | >3 | 3240-3130 | 1700-1640 |
| 3 | >30 | 3230-3120 | 1660-1630 |
| 4 | >5 | 3230-3130 | 1630-1590 |
| 5 | >20 | 3240-3200 | 1640-1610 |
| 6 | >20 | 3200-3130 | 1660-1630 |
| 7 | >20 | 3220-3140 | 1680-1620 |
| 8 | >15 | 3230-3120 | 1670-1610 |

*Solubility in physiological saline solution

In view of the fact that cis-Platin has solubility of about 1.2 mg/ml in physiological saline solution, the present compounds apparently have high solubility in water. In addition, the present compounds are dissolved in water quickly. Therefore, when used as an injection, the crystals of the present compounds can be dissolved in water prior to administration and the resulting aqueous solutions can be administered immediately after dissolution.

Next, the antitumor activities of the present compounds will be described by way of Experimental Examples.

EXPERIMENTAL EXAMPLE 1

Test of growth inhibitory activity against various kinds of cultured tumor cells (Test method)

Mouse leukemia L1210 cells were cultured in a RPMI 1640 medium containing 10% of fetal calf serum and mouse Lewis lung carcinoma (LL) cells were cultured in a RPMI 1640 medium containing 10% fetal calf serum and 100 μg/ml of Kanamycin. Inhibition percentage (%) of growth on each tumor cells was calculated from the number of cells in the cases of addition and no addition of each compound, and $IC_{50}$ value (a concentration at which growth was inhibited by 50%) was obtained from a graph prepared by plotting a concentration of compounds and the inhibition percentage on logarithmic probability paper.

The results are shown in Table 2.

TABLE 2

| Compound No. | IC$_{50}$ (μg/ml) | |
| --- | --- | --- |
| | Tumor cell L1210 | Tumor cell LL |
| 1 | 0.04 | 0.43 |
| 2 | 0.11 | 0.65 |
| 3 | 0.27 | 0.95 |
| 4 | 1.01 | 2.10 |
| 5 | 0.40 | 1.06 |
| 6 | 0.11 | 1.06 |

As is obvious from Table 2, the compounds of the present invention show an inhibition activity on the growth of tumor cells at a low concentration.

The present compounds show an excellent inhibition activity also on the growth of cis-Platin resistant tumor cells which have acquired a resistance to cis-Platin as a result of its administration. An experimental example on this activity will be described as follows.

EXPERIMENTAL EXAMPLE 2

Test of growth inhibitory activity against cis-Platin resistant tumor cells (Test method)

$1 \times 10^5$ mouse leukemia L1210 cells or $1 \times 10^5$ mouse leukemia P388 cells were inoculated into the abdominal cavities of CDF$_1$ female mice. After 2 days from the inoculation, 6 mg/kg of cis-Platin was administered to them intraperitoneally. After 5 days, their tumor cells were inoculated to the abdominal cavities of other CDF$_1$ female mice, and the same treatment was applied. By repeating this procedure, cis-Platin resistant tumor cells were obtained.

Using the tumor cells thus obtained, a test for growth inhibition activity was conducted in the same manner as in Experimental Example 1, whereby IC$_{50}$ for cis-Platin resistant tumor cells (hereinafter referred to as IC$_{50}$R) was obtained. Then, the ratio of this IC$_{50}$R to IC$_{50}$ for tumor cells having no cis-Platin resistance, namely, IC$_{50}$R/IC$_{50}$ was calculated.

The results are shown in Table 3.

TABLE 3

| Compound No. | IC$_{50}$R/IC$_{50}$ | |
| --- | --- | --- |
| | Tumor cell L1210 | Tumor cell P388 |
| cis-Platin | 18.0 | 8.0 |
| 3 | 1.3 | 4.6 |
| 5 | 1.4 | 6.2 |

As is obvious from Table 3, the present compounds show an inhibition activity also on the growth of cis-Platin resistant tumor cells at a low concentration.

EXPERIMENTAL EXAMPLE 3

Test of antitumor activity against mouse leukemia L1210 in vivo (Test method)

$1 \times 10^5$ mouse leukemia L1210 cells were inoculated into the abdominal cavities of 6-week-old female CDF$_1$ mice. From the next day, a compound was administered to them intraperitoneally once a day for 5 consecutive days. Mice of a compound-non-treated group (control group) were administered with physiological saline solution in the same manner. The mean survival time of the compound-treated group and the control group were measured and T/C was calculated from the equation (1):

$$\frac{T}{C} = \frac{\text{Mean survival time of compound-treated group}}{\text{Mean survival time of control group}} \times 100 \quad (1)$$

When any mouse died during the test due to the acute toxicity of the compound administered, 50% lethal dose (LD$_{50}$) was calculated according to the conventional method.

The results are shown in Table 4. In Table 4, max (T/C) means the maximum value of T/C and optimum doses (Op. dose) means a daily administration amount giving the max (T/C), namely, an optimum daily administration amount.

TABLE 4

| Compound No. | max (T/C) | Opt. dose (mg/kg) | LD$_{50}$ (mg/kg) |
| --- | --- | --- | --- |
| 1 | 323 | 2.0 | 3.0 |
| 2 | 296 | 4.0 | 7.2 |
| 3 | 400 | 16.0 | — |
| 4 | 328 | 32.0 | — |
| 5 | 245 | 32.0 | — |

As is obvious from Table 4, the compounds of the invention have a life prolongation effect for mice inoculated with mouse leukemia L1210 cells.

The compounds of the present invention have life prolongation effects also for mice inoculated with tumor cells other than mouse leukemia L1210 cells. These effects will be explained in Experimental Example 4.

EXPERIMENTAL EXAMPLE 4

Test of antitumor activity against mouse Lewis lung carcinoma (Test method)

$1 \times 10^6$ mouse Lewis lung carcinoma cells were inoculated into the abdominal cavities of 6-week-old male BDF$_1$ mice. From the next day, a compound was administered to them intraperitoneally once a day for 5 consecutive days. Mice of compound-non-treated group (control group) were administred with physiological saline solution in the same manner. From the median survival time of the compound-treated group and the control group, T/C was calculated according to the following equation (2):

$$\frac{T}{C} = \frac{\text{Mean survival time of compound-treated group}}{\text{Median survival time of control group}} \times 100 \quad (2)$$

The results are shown in Table 5. In Table 5, max (T/C), and Opt. dose and LD$_{50}$ mean the same ones in Table 4, respectively.

TABLE 5

| Compound No. | max (T/C) | Opt. dose (mg/kg) | LD$_{50}$ (mg/kg) |
| --- | --- | --- | --- |
| 3 | 234 | 32.0 | — |
| 4 | 144 | 32.0 | 48.0 |

As is obvious from Table 5, the compounds of the invention have a life prolongation effect for mice inoculated with mouse Lewis lung carcinoma cells.

Next, the renal toxicity of the present compounds will be described by way of an Experimental Example.

EXPERIMENTAL EXAMPLE 5

Test of renal toxicity (Test method)

A compound was singly administered to 6-week-old male $CDF_1$ mice intraperitoneally. After 4 days, their blood was collected for measurement of blood urea nitrogen concentration (BUN value).

The results are shown in Table 6. The optimum dose of cis-Platin was 4 mg/kg according to the test method of Example 3, but in this renal toxicity test, a BUN value which is much higher than the normal value (30 mg/dl or lower) was seen when cis-Platin wa administered in an amount of four times of the optimum dose. Based on this fact, as shown in Table 6, the administration amount of the present compound employed in this Experimental Example was fixed to four times of the optimum dose obtained in Experimental Example 3. In Table 6, body weight ratio is a ratio of body weight on the fourth day from administration to body weight on the administration day.

TABLE 6

| Compound No. | Administration amount (mg/kg) | Body weight ratio | BUN value (mg/dl) |
|---|---|---|---|
| Physiological saline solution | — | 1.05 | 22.7 |
| cis-Platin | 16 | 0.72 | 92.9 |
| 1 | 8 | 0.79 | 12.7 |
| 2 | 16 | 0.77 | 11.2 |
| 3 | 64 | 1.00 | 26.4 |
| 4 | 128 | 0.89 | 16.4 |
| 5 | 128 | 0.89 | 18.8 |

As is obvious from Table 6, the values obtained when the present compounds were administered are very lower than the value obtained when commercially available cis-Platin was administered, and are close to the value obtained when physiological saline solution was administered. This indicates that the present compounds have very low renal toxicity. Accordingly, the present compounds can be used as antitumor agents with very low renal toxicity. In view of this characteristic and high solubility in water, the present compounds, when intravenously injected, can be applied not only in continuous administration but also in bolus administration.

Some of the present compounds have, as a ligand, a diamine having an asymmetric carbon atom. Those optical isomers obtained by optical resolution, can be applied as same as the racemic ones.

The compounds of the present invention show growth inhibition activities on the tumor cells at low concentrations and accordingly have very excellent antitumor effects against various kinds of tumors. The present compounds have high solubility in water and are quickly dissolved in water. The present compounds have low renal toxicity and low vomiting toxicity. Further, the present compounds are mild with respect to bone marrow toxicity which is generally seen with the conventional platinum complex antitumor agents; that is, the decrease in the number of white blood cells occurs mainly and their toxicity to platelets is very slight. Furthermore, recovery to normal conditions is very rapid and accordingly control is easy when the present compounds are used as an antitumor agent. Based on the fact, the present compounds can be used as an excellent antitumor agent. Moreover, the present compounds are stable in air at room temperature, thus requiring no low temperature storage.

What is claimed is:

1. A diamine platinum (II) complex represented by the formula:

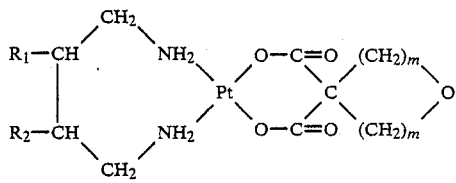

wherein $R_1$ and $R_2$ are each a $C_1$–$C_4$ alkyl group and wherein both occurrences of m are 1 or 2.

2. A diamine platinum (II) complex according to claim 1 wherein R1 and R2 are each a methyl group.

3. A diamine platinum (II) complex according to claim 1, wherein m is 2, represented by

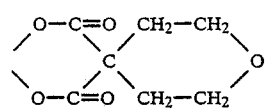

4. cis-4-Oxacyclohexane-1,1-dicarboxylato-2,3-dimethyl 1,4-butanediamine platinum.

* * * * *